United States Patent
Deng et al.

(10) Patent No.: US 11,918,713 B2
(45) Date of Patent: Mar. 5, 2024

(54) HIGH-TEMPERATURE NEGATIVE-PRESSURE AIR EXCHANGE STERILIZER AND STERILIZATION METHOD THEREOF

(71) Applicant: Harbin Institute of Technology, Harbin (CN)

(72) Inventors: Zongquan Deng, Harbin (CN); Qiquan Quan, Harbin (CN); Dewei Tang, Harbin (CN); Rongqiang Liu, Harbin (CN); Zhong Zheng, Harbin (CN); Xiao Li, Harbin (CN)

(73) Assignee: HARBIN INSTITUTE OF TECHNOLOGY, Harbin (CN)

( * ) Notice: Subject to any disclaimer, the term of this patent is extended or adjusted under 35 U.S.C. 154(b) by 320 days.

(21) Appl. No.: 17/334,857

(22) Filed: May 31, 2021

(65) Prior Publication Data
US 2021/0290813 A1    Sep. 23, 2021

(30) Foreign Application Priority Data
Dec. 16, 2020    (CN) .......................... 202011484637.4

(51) Int. Cl.
*A61L 9/16*    (2006.01)
(52) U.S. Cl.
CPC ............ *A61L 9/16* (2013.01); *A61L 2209/111* (2013.01); *A61L 2209/14* (2013.01)
(58) Field of Classification Search
CPC ....................................................... A61L 9/16
See application file for complete search history.

(56) References Cited

U.S. PATENT DOCUMENTS

2005/0211415 A1*    9/2005    Arts ....................... B01D 46/62
                                                             165/59

FOREIGN PATENT DOCUMENTS

| CN | 111457535 A | 7/2020 |
| CN | 111854027 A | 10/2020 |

* cited by examiner

Primary Examiner — Timothy C Cleveland
(74) Attorney, Agent, or Firm — IPRO, PLLC

(57) ABSTRACT

The present disclosure provides a high-temperature negative-pressure air exchange sterilizer and a sterilization method thereof. An air inlet is disposed at a bottom of a waterproof shell of the sterilizer, and an inlet filter is installed at the air inlet. Air entering from the air inlet is divided into two paths at a check valve. One path is connected with a negative-pressure fan through a pipeline B, and the other path is communicated with an air outlet through a pipeline A. A plurality of heating rods and temperature sensors are disposed in the pipeline A. The pipeline A is zigzag disposed at an upper part of the waterproof shell, and a thermal insulation material is disposed outside a zigzag part. A butterfly valve and an outlet filter screen are sequentially disposed at the air outlet in an air exhaust direction. The problem that viruses exhaled by breathing of an infected person are mixed in aerosol, so that a person in close contact with the infected person is likely to be infected is solved. According to the present disclosure, polluted air is heated through a plurality of sections of high-temperature areas, and finally viruses are killed in a pipe, so that clean air is exhausted to the external environment; the negative-pressure fan is used to form a certain negative pressure in a room to complete an indoor air exchange; the viruses are killed quickly; and the virus killing efficiency is high.

6 Claims, 8 Drawing Sheets

HIGH-TEMPERATURE NEGATIVE-PRESSURE AIR EXCHANGE STERILIZER AND STERILIZATION METHOD THEREOF

TECHNICAL FIELD

The present disclosure relates to a high-temperature negative-pressure air exchange sterilizer and a sterilization method thereof, and belongs to the technical field of sterilization equipment.

BACKGROUND

The epidemic virus has strong transmissibility and seriously endangers human health. In recent years, massive outbreaks of avian influenza virus, SARS coronavirus and 2019 novel coronavirus result in the loss of a large number of precious lives or serious bodily injury. Common signs of human infection with coronavirus include respiratory symptoms, fever, cough, shortness of breath and dyspnea. In more severe cases, infection can lead to pneumonia, severe acute respiratory syndrome, renal failure, and even death. The transmission characteristics of the epidemic virus are high infectivity and high concealment, and the main transmission way is aerosol transmission. Aerosol refers to a gaseous dispersion system composed of solid or liquid particles suspending in a gaseous medium. Solid and liquid particles in the atmosphere do Brownian motion, do not settle due to gravity, and can suspend in the atmosphere for as long as several months. Viruses exhaled by breathing of an infected person are mixed in aerosol, and easy to cause infection to people in close contact.

SUMMARY

In order to solve the problem mentioned in the Background above that viruses exhaled by breathing of an infected person are mixed in aerosol, and easy to cause infection to people in close contact, the present disclosure provides a high-temperature negative-pressure air exchange sterilizer.

The present disclosure provides a high-temperature negative-pressure air exchange sterilizer, including a differential pressure control valve, an air inlet, an inlet filter, a check valve, a negative-pressure fan, a pipeline A, a pipeline B, a thermal insulation material, a plurality of heating rods, a plurality of temperature sensors, a butterfly valve, an outlet filter screen, an air outlet and a waterproof shell. The air inlet is disposed at a bottom of the waterproof shell, and the inlet filter is installed at the air inlet. Air entering from the air inlet is divided into two paths at the check valve. One path is connected with the negative-pressure fan through the pipeline B, and the other path is communicated with the air outlet through the pipeline A. The plurality of heating rods are disposed in the pipeline A. A temperature sensor is disposed beside each of the heating rods. The pipeline A is zigzag disposed at an upper part of the waterproof shell, and the thermal insulation material is disposed outside a zigzag part. The butterfly valve and the outlet filter screen are sequentially disposed at the air outlet in an air exhaust direction.

Preferably, the differential pressure control valve includes a filter, a one-way valve and a differential pressure gauge. The filter is disposed at an air inlet of the differential pressure control valve, and the one-way valve controls opening and closing of the air inlet.

Preferably, the differential pressure gauge is configured to detect indoor and outdoor differential pressure. When the differential pressure exceeds a set range of the differential pressure gauge, the one-way valve is opened, and outdoor air enters a room after being filtered by the filter.

Preferably, a temperature controller is further installed in the waterproof shell. The temperature controller receives a temperature control instruction of a controller, controls on and off of the plurality of heating rods, collects signals of the plurality of temperature sensors, and completes a temperature closed-loop control at a heating point.

Preferably, a driver is further installed in the waterproof shell. The driver receives a rotating speed instruction of the controller to control the negative-pressure fan to work at a set rotating speed.

Preferably, the controller is further installed in the waterproof shell. The controller, as a master control system of a sterilizer body, is configured to process electric signals fed back by each sensor, and meanwhile send a corresponding instruction to control each electrical apparatus element to work according to a designed program.

Preferably, the temperature sensor collects air temperature values and feeds the air temperature values back to the temperature controller. The heating rod is controlled to be powered on or off according to fed-back temperature values, to complete a closed-loop control over air temperature of a heating unit.

Preferably, sterilization time of the high-temperature negative-pressure air exchange sterilizer is <3 s.

Preferably, sterilization temperatures of the plurality of heating rods are set in a stepped manner, so that service life of a heating unit is prolonged, and equipment safety is improved.

A sterilization method of a high-pressure negative-pressure air exchange sterilizer specifically includes the following steps:

(1) after the high-temperature negative-pressure air exchange sterilizer is started, controlling, by a controller, the temperature controller to power on heating rods, according to a set sterilization temperature, and meanwhile collecting, by the temperature sensor, temperature signals and feeding the temperature signals back to the temperature controller and the controller; after a temperature reaches a sterilization requirement, controlling, by the controller, the driver to start the negative-pressure fan, so that air enters from the air inlet, and passes through the inlet filter, the check valve and the negative-pressure fan to enter the pipeline A; disposing the plurality of heating rods in the pipeline A, so that air passes through the plurality of heating rods, and is instantly heated to a set temperature to achieve a purpose of high-temperature sterilization; meanwhile, feeding, by the temperature sensor, the collected air temperature signals back to the temperature controller and the controller, and exhausting sterilized air out of a room through the butterfly valve, the outlet filter screen and the air outlet; and (2) when the collected temperature signals exceed a set value, controlling, by the controller, the temperature controller to power off the heating rods to reduce the temperature; and when the collected temperature signals are lower than the set value, controlling, by the controller, the temperature controller to power on the heating rods to raise the temperature.

The high-temperature negative-pressure air exchange sterilizer and the sterilization method thereof according to the present disclosure have the beneficial effects:

1. According to the high-temperature negative-pressure air exchange sterilizer of the present disclosure, polluted air is heated through a plurality of sections of high-temperature areas, and finally viruses are killed in a pipe, so that clean air is exhausted to the external environment.

2. According to the high-temperature negative-pressure air exchange sterilizer of the present disclosure, a negative pressure generator is adopted to exhaust indoor air outwards, and form a certain negative pressure in a room to complete an indoor air exchange.

3. According to the high-temperature negative-pressure air exchange sterilizer of the present disclosure, the check valve is adopted to isolate indoor polluted air from an outdoor space, so that the air exhausted to the outdoor space is ensured to be safe, pollution-free and high in safety.

4. According to the high-temperature negative-pressure air exchange sterilizer of the present disclosure, in order to prolong the residence time of air in the pipe, the pipe is provided with a certain length; and a plurality of heating rods are disposed in the pipe, and the temperatures of the plurality of heating rods are set in a stepped manner, so that the service life of the heating unit is prolonged, and equipment safety is improved.

5. According to the high-temperature negative-pressure air exchange sterilizer of the present disclosure, instant virus killing can be achieved by cooperation of the plurality of heating rods and the negative-pressure fan; the viruses are killed quickly, and the virus killing efficiency is high.

BRIEF DESCRIPTION OF FIGURES

The accompanying drawings constituting a part of the present application serve to provide a further understanding of the present disclosure, and illustrative examples of the present disclosure and descriptions thereof serve to explain the present disclosure and do not constitute an undue limitation of the present disclosure.

In the accompanying drawings.

Figure 1:
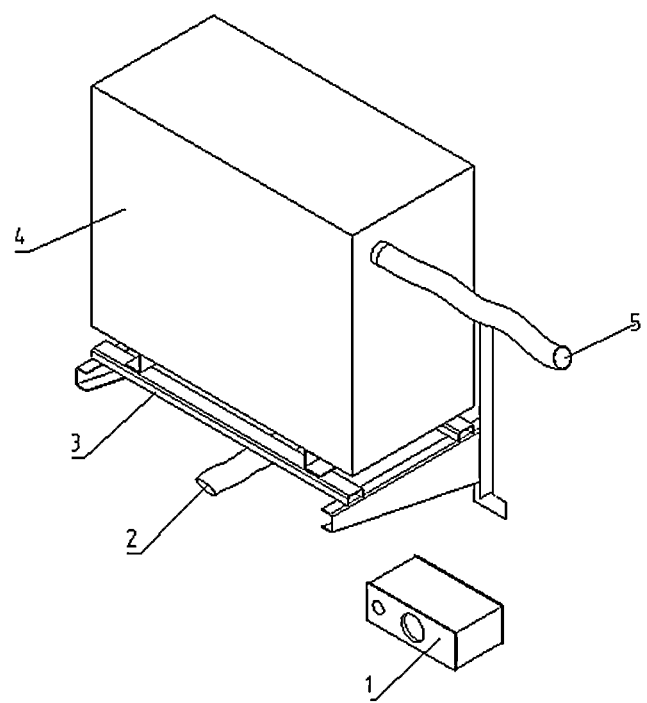
FIG. 1 is a space diagram of an external structure of a high-temperature negative-pressure air exchange sterilizer according to the present disclosure.

In the figures: 1 denotes a pressure differential control valve, 2 denotes an air intake pipe, 3 denotes a fixing support, 4 denotes a sterilizer body, 5 denotes an air exhaust pipe, 6 denotes an air inlet, 7 denotes an inlet filter, 8 denotes a check valve, 9 denotes a negative-pressure fan, 10 denotes a pipeline A, 25 denotes a pipeline B, 11 denotes a thermal insulation material, 12 denotes a heating rod, 13 denotes a temperature sensor, 14 denotes a butterfly valve, 15 denotes an outlet filter screen, 16 denotes an air outlet, 17 denotes a waterproof shell, 18 denotes a temperature controller, 19 denotes a driver, 20 denotes a controller, 21 denotes a high-temperature negative-pressure air exchange sterilizer, 22 denotes a filter, 23 denotes a one-way valve, and 24 denotes a differential pressure gauge.

DETAILED DESCRIPTION

Embodiments of the present disclosure are further described in detail below with reference to the accompanying drawings:

Embodiment I: the present embodiment is described by referring to FIGS. 1-8. A high-temperature negative-pressure air exchange sterilizer according to the present embodiment includes a differential pressure control valve 1, an air inlet 6, an inlet filter 7, a check valve 8, a negative-pressure fan 9, a pipeline A 10, a pipeline B 25, a thermal insulation material 11, a plurality of heating rods 12, a plurality of temperature sensors 13, a butterfly valve 14, an outlet filter screen 15, an air outlet 16 and a waterproof shell 17. The differential pressure control valve 1 is installed on a wall body to control outdoor air to enter a room.

The air inlet 6 is disposed at a bottom of the waterproof shell 17, and the inlet filter 7 is installed at the air inlet 6. Air entering from the air inlet 6 is divided into two paths at the check valve 8. One path is connected with the negative-pressure fan 9 through the pipeline B 25, and the other path is communicated with the air outlet 16 through the pipeline A 10. The plurality of heating rods 12 are disposed in the pipeline A 10, and the temperature sensor 13 is disposed beside each of the heating rods 12. The pipeline A 10 is zigzag disposed at an upper part of the waterproof shell 17, and the thermal insulation material 11 is disposed outside a zigzag part. The butterfly valve 14 and the outlet filter screen 15 are sequentially disposed at the air outlet 16 in an air exhaust direction.

The differential pressure control valve 1 includes a filter 22, a one-way valve 23 and a differential pressure gauge 24. The filter 22 is disposed at an air inlet of the differential pressure control valve 1, and the one-way valve 23 controls opening and closing of the air inlet.

The differential pressure gauge 24 is configured to detect indoor and outdoor differential pressure. When the differential pressure exceeds a set range of the differential pressure gauge 24, the one-way valve 23 is opened, and outdoor air enters a room after being filtered by the filter 22.

A temperature controller 18 is further installed in the waterproof shell 17. The temperature controller 18 receives a temperature control instruction of a controller 20, controls on and off of the plurality of heating rods 12, collects signals of the plurality of temperature sensors 13, and completes a temperature closed-loop control at a heating point.

A driver 19 is further installed in the waterproof shell 17. The driver 19 receives a rotating speed instruction of the controller 20 to control the negative-pressure fan 9 to work at a set rotating speed.

The controller 20 is further installed in the waterproof shell 17. The controller 20, as a master control system of a sterilizer body, is configured to process electric signals fed back by each sensor, and meanwhile send a corresponding instruction to control each electrical apparatus element to work according to a designed program.

The effect of the butterfly valve 14: the butterfly valve can completely seal a pipe in a shutdown state, to prevent gas in the pipe from leaking out, thereby improving equipment safety.

A heating unit: the heating unit is composed of the temperature sensors 13 and the heating rods 12. The heating rods 12 enable the temperature of air flowing through the heating unit to be raised to a set temperature of the temperature controller within a short time (3 s). The temperature sensors 13 collect air temperature values and feed the air temperature values back to the temperature controller 18. The heating rods 12 are controlled to be powered on or off according to the fed-back temperature values, to achieve a closed-loop control over air temperature of the heating unit.

The differential pressure control valve 1 is configured to control a channel and outside air flows into a room through the channel. Indoor air is ensured to have a certain negative pressure by controlling one-way flow.

The working principle of the differential pressure control valve 1: the differential pressure control valve 1 is installed on a wall body. The differential pressure gauge 24 is set to measure a negative pressure value. After the high-temperature negative-pressure air exchange sterilizer is started, a certain negative pressure will be generated indoors and outdoors due to the fact that an indoor space is closed, and an indoor and outdoor differential pressure is detected by the differential pressure gauge 23. When the differential pressure exceeds a set range of the differential pressure gauge 24, the one-way valve 23 is opened, and outdoor air enters a room after being filtered by the filter 22.

The specific working process of the high-temperature negative-pressure air exchange sterilizer is as follows:

As shown in FIG. 1, the high-temperature negative-pressure air exchange sterilizer includes a differential pressure control valve 1, an air intake pipe 2, a fixing support 3, a sterilizer body 4 and an air exhaust pipe 5. The fixing support 3 is configured to fix the sterilizer body 4 to a wall body, and the air intake pipe 2 and the air exhaust pipe 5 are installed on the sterilizer body 4. Meanwhile, the indoor space is in communication with the sterilizer body 4 through the air intake pipe 2. The differential pressure control valve 1 is installed on the wall to control outdoor air to enter a room.

Figure 2:
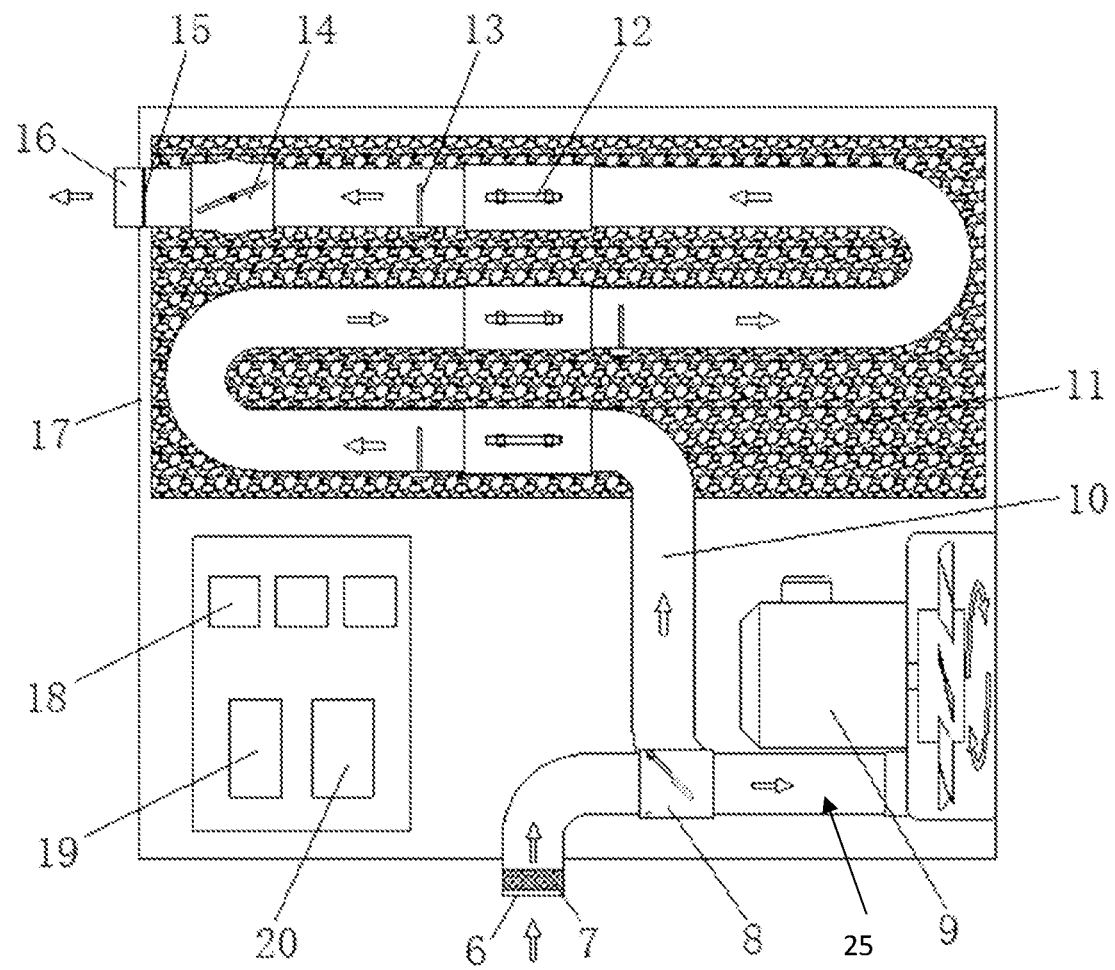
FIG. 2 is a schematic diagram of an internal structure of a high-temperature negative-pressure air exchange sterilizer according to the present disclosure, wherein arrows indicate a gas flow direction.

As shown in FIG. 2, after the high-temperature negative-pressure air exchange sterilizer is started, the controller 20 controls the temperature controller 18 to power on the heating rod 12 according to a set sterilization temperature, and meanwhile the temperature sensor 13 collects temperature signals and feed the temperature signals back to the temperature controller 18 and the controller 20. After the temperature reaches a sterilization requirement, the controller 20 controls the driver 19 to start the negative-pressure fan 9. Air enters from the air inlet 6, and passes through the inlet filter 7, the check valve 8 and the negative-pressure fan 9 to enter the pipeline 10. One or more heating rods 12 are disposed in the pipeline 10. Air passes through the plurality of heating rods 12, and is heated within a very short time to a temperature set by the temperature controller, so as to achieve a purpose of high-temperature sterilization. Meanwhile, the temperature sensor 13 feeds the collected air temperature signals back to the temperature controller 18 and the controller 20. Sterilized air is exhausted out of a room through the butterfly valve 14, the outlet filter screen 15 and the air outlet 16.

When the collected temperature signals exceed a set value, the controller 20 controls the temperature controller 18 to power off the heating rods 12 to reduce temperature. When the collected temperature signals are lower than the set value, the controller 20 controls the temperature controller 18 to power on the heating rods 12 to raise the temperature.

In order to prolong the residence time of air in the pipe, the pipe is provided with a certain length. The plurality of heating rods 12 are disposed in the pipe, and the temperatures of the plurality of heating rods 12 are set in a stepped manner, so that the service life of the heating unit is prolonged, and equipment safety is improved.

After the negative-pressure fan 9 is started, indoor air is sucked into the sterilizer body, and a certain negative pressure is produced indoors. After an indoor negative pressure value is greater than a set value of the differential pressure gauge 24, the one-way valve 23 is opened, and outdoor air is filtered by the filter 22 and enters a room to complete indoor and outdoor air exchange. When the negative pressure value is smaller than the set value of the differential pressure gauge 24, the one-way valve 23 is closed.

Figure 3:
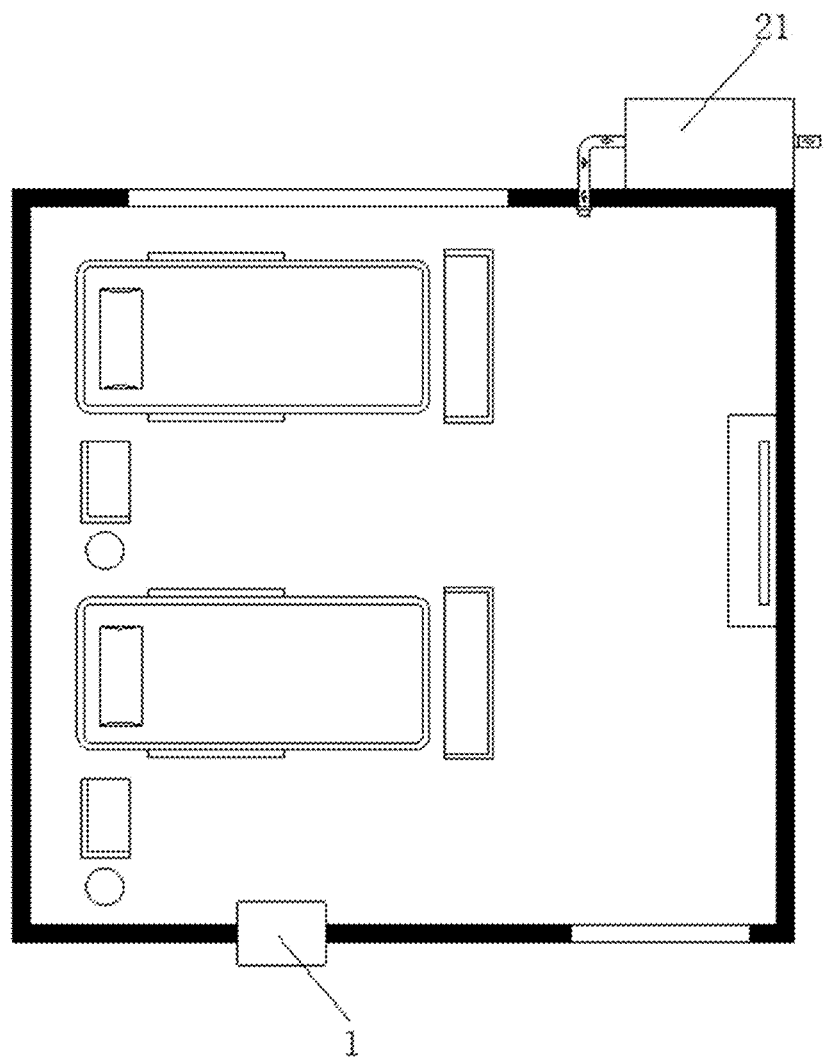
FIG. 3 is a schematic diagram of a high-temperature negative-pressure air exchange sterilizer according to the present disclosure applied to a hospital scene.

The application of the high-temperature negative-pressure air exchange sterilizer includes:

As shown in FIG. 3, in an epidemic prevention hospital, a high-temperature negative-pressure air exchange sterilizer 21 is installed on an outer wall of each isolated ward. Inside the isolated ward polluted by air exhaled by an isolated patient, the polluted air is extracted by the sterilizer, and flows through a high-temperature area in the sterilizer to thoroughly kill viruses, and then the air is exhausted to outdoor atmosphere.

Figure 4:
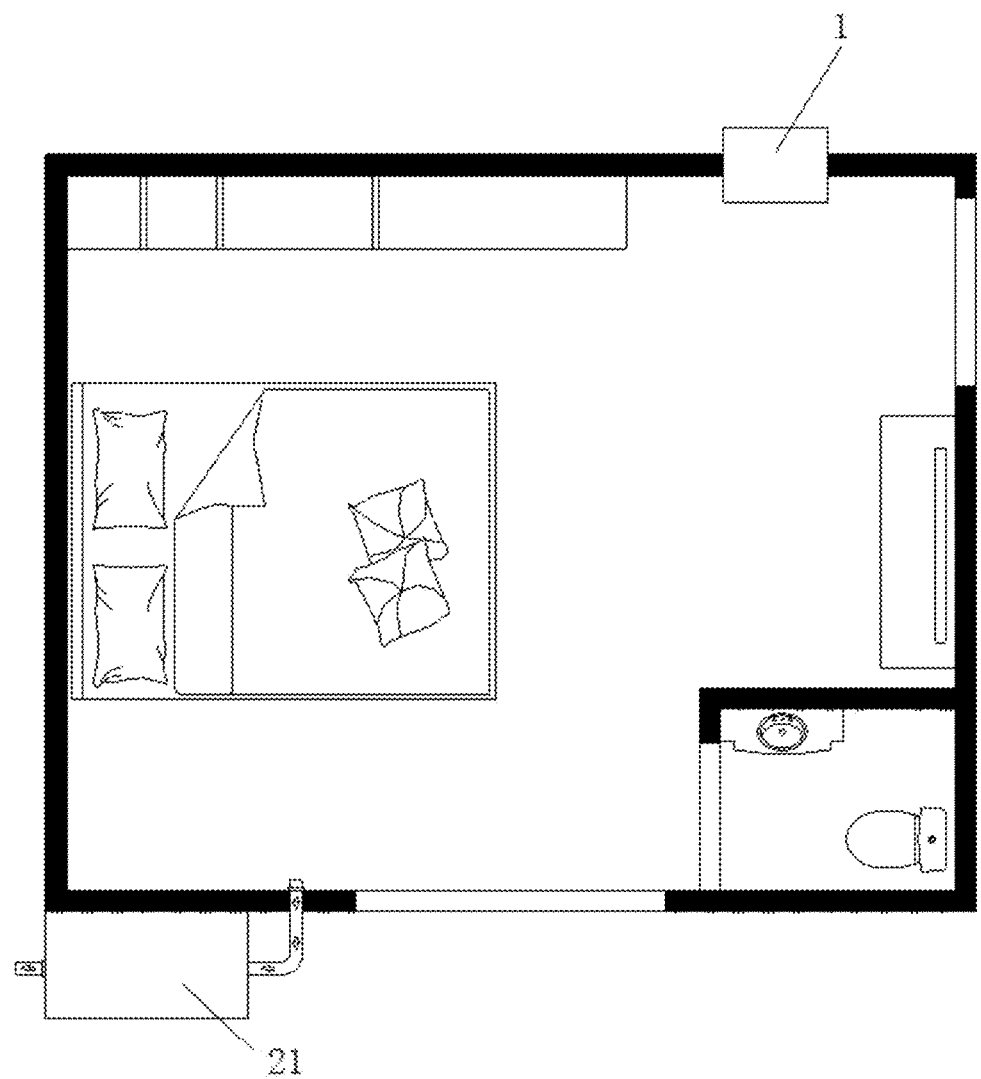
FIG. 4 is a schematic diagram of a high-temperature negative-pressure air exchange sterilizer according to the present disclosure applied to a high-grade residential scene.

As shown in FIG. 4, a room called a health care room is independently developed in a high-grade residence. A high-temperature negative-pressure air exchange sterilizer 21 is installed on an outer wall. The room is used for normal living at ordinary times, and once a family member has infection symptoms and feels uncomfortable, the family member enters the health care room for living. The health care room is closed to ensure airtightness. The high-temperature air exchange sterilizer is started to exchange and sterilize air in the room. An article exchange window is disposed on the wall of the health care room and configured to convey articles of daily use for the isolated family member in the health care room.

Figure 5:
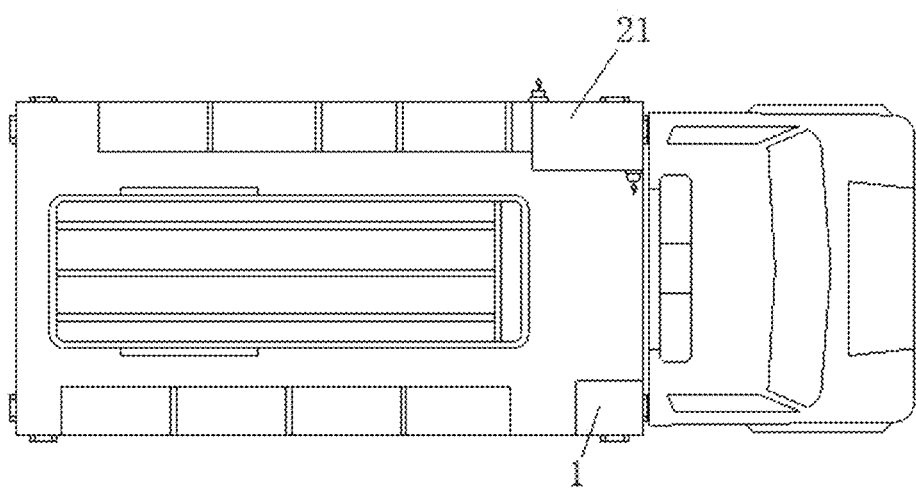
FIG. 5 is a schematic diagram of a high-temperature negative-pressure air exchange sterilizer according to the present disclosure applied to an ambulance scene.

As shown in FIG. 5, a medical vehicle such as an ambulance is provided with a high-temperature negative-pressure air exchange sterilizer for sterilizing air in the ambulance and completing air exchange.

Figure 6:
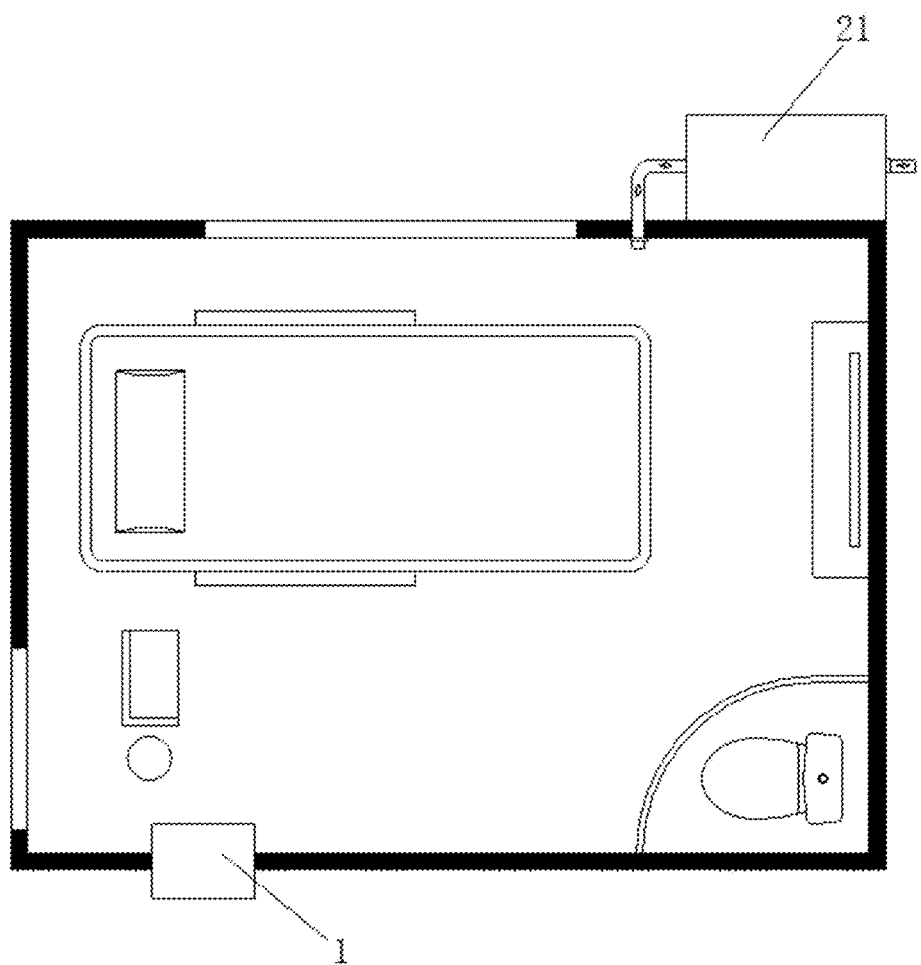
FIG. 6 is a schematic diagram of a high-temperature negative-pressure air exchange sterilizer according to the present disclosure applied to an isolation room scene.
Figure 7:
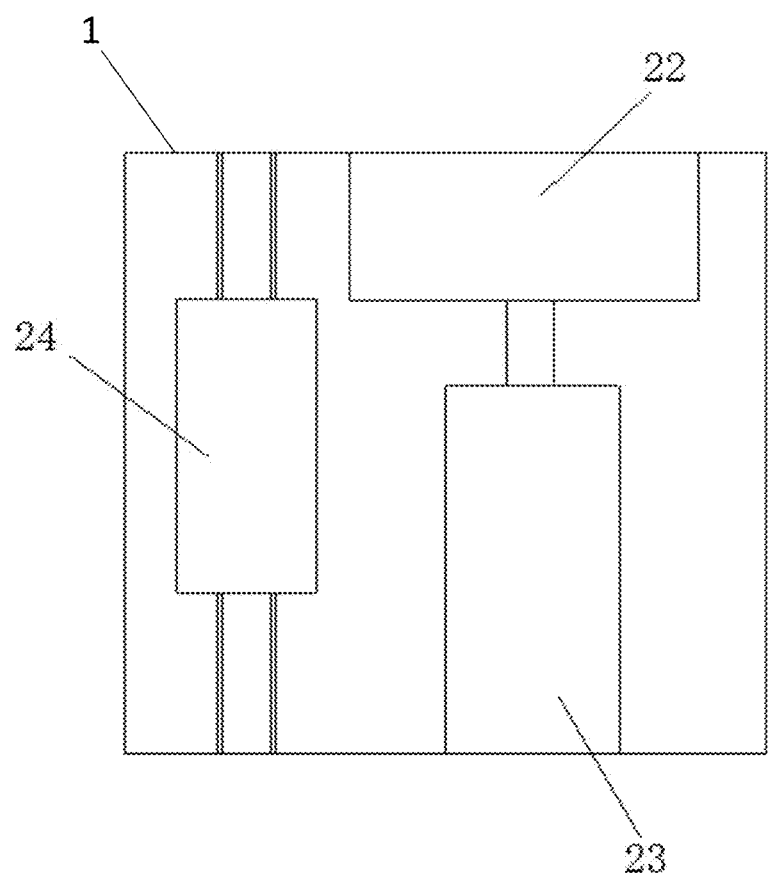
FIG. 7 is a schematic structure diagram of a differential pressure control valve according to the present disclosure.
Figure 8:
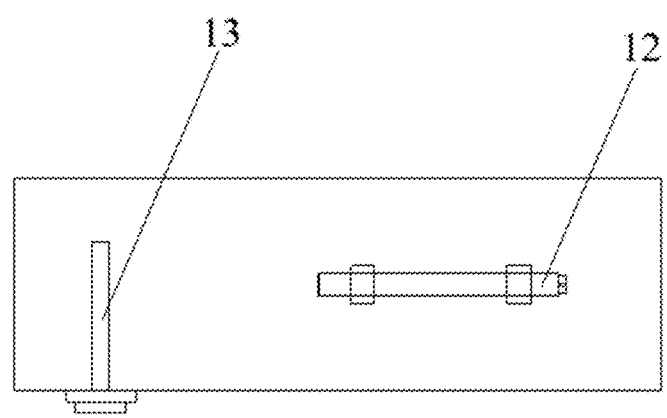
FIG. 8 is a partial enlarged view of a heating rod and a temperature sensor.

As shown in FIG. 6, in airports, stations and schools, epidemic protection isolated rooms are commonly disposed. High-temperature negative-pressure air exchange sterilizers are disposed on outer walls of the isolated rooms to complete sterilization and air exchange of indoor air.

The objective, technical solutions and beneficial effects of the present disclosure are further described in detail with reference to the above specific examples. It should be understood that the foregoing descriptions are only specific examples of the present disclosure, are not intended to limit the present disclosure, and may also be a reasonable combination of the characteristics recorded in each of the above embodiments. Any modification, equivalent replacement, improvement and the like made within the spirit and principle of the present disclosure shall be included in the protection scope of the present disclosure.

What is claimed is:

1. A system for air exchange and sterilization in a room, the system comprising:
   a high-temperature negative-pressure air exchange sterilizer (21) arranged to exhaust indoor air out of the room, and
   a differential pressure control valve (1) arranged to introduce outdoor air into the room, wherein the high-temperature negative-pressure air exchange sterilizer (21) comprises a first air inlet (6), an inlet filter (7), a check valve (8), a negative-pressure fan (9), pipeline A (10), pipeline B (25), a thermal insulation material (11), a plurality of heating rods (12), a plurality of temperature sensors (13), a butterfly valve (14), an outlet filter screen (15), an air outlet (16) and a waterproof shell (17), the first air inlet (6) is disposed at a bottom part of the waterproof shell (17) to introduce indoor air into the high-temperature negative-pressure air exchange sterilizer (21);

the inlet filter (7) and the check valve (8) are installed at the first air inlet (6);

air entering from the air inlet (6) passes through the inlet filter (7), and is divided into a first path and a second path at the check valve (8), the first path is communicated with the negative-pressure fan (9) through a pipeline B (25), and a second path is communicated with the air outlet (16) through the pipeline A (10);

the plurality of heating rods (12) are disposed in the pipeline A (10);

one temperature sensor of the plurality of temperature sensors (13) is disposed beside each of the plurality of heating rods (12);

the pipeline A (10) is zigzag disposed at an upper part of the waterproof shell (17);

the thermal insulation material (11) is disposed outside a zigzag part; and the butterfly valve (14) and the outlet filter screen (15) are sequentially disposed at the air outlet (16) in an air exhaust direction;

the sterilization temperatures of the plurality of heating rods (12) are set in a stepped manner, so that service life of a heating unit is prolonged, and equipment safety is improved;

the differential pressure control valve (1) is installed on a wall body of the room, and separate from the high-temperature negative-pressure air exchange sterilizer (21), and comprises a filter (22), a one-way valve (23) and a differential pressure gauge (24); the filter (22) is disposed at second air inlet of the differential pressure control valve (1); and the one-way valve (23) controls opening and closing of the second air inlet; and the differential pressure gauge (24) is configured to detect indoor and outdoor differential pressure; and when the differential pressure exceeds a set range of the differential pressure gauge (24), the one-way valve (23) is opened, and outdoor air is filtered by the filter (22) and then enters into the room.

2. The system according to claim 1, wherein a controller (20) is further installed in the waterproof shell (17), and the controller (20), as a master control system of the high-temperature negative-pressure air exchange sterilizer (21), is configured to process electric signals fed back by each of the plurality of temperature sensors, and meanwhile send a corresponding instruction to control the high-temperature negative-pressure air exchange sterilizer (21) to work according to a designed program.

3. The system according to claim 2, wherein a temperature controller (18) is further installed in the waterproof shell (17); and the temperature controller (18) receives a temperature control instruction of the controller (20), controls on and off of the plurality of heating rods (12), collects signals of the plurality of temperature sensors (13), and completes a temperature closed-loop control at a heating point.

4. The system according to claim 2, wherein a driver (19) is further installed in the waterproof shell (17), and the driver (19) receives a rotating speed instruction of the controller (20) to control the negative-pressure fan (9) to work at a set rotating speed.

5. The system according to claim 3, wherein the plurality of temperature sensors (13) collect air temperature values and feed the air temperature values back to the temperature controller (18), and the plurality of heating rods (12) are controlled to be powered on or off according to the fed-back temperature values.

6. The system according to claim 1, wherein sterilization time of the high-temperature negative-pressure air exchange sterilizer is less than 3 s.

* * * * *